(12) United States Patent
Costantino et al.

(10) Patent No.: US 7,282,216 B2
(45) Date of Patent: Oct. 16, 2007

(54) BIOCOMPATIBLE POLYMER BLENDS AND USES THEREOF

(75) Inventors: Henry R. Costantino, Newton, MA (US); Mark A. Tracy, Arlington, MA (US); Kevin L. Ward, Arlington, MA (US); Wendy W. Nelson, Foxboro, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 604 days.

(21) Appl. No.: 10/293,974

(22) Filed: Nov. 12, 2002

(65) Prior Publication Data

US 2003/0133980 A1    Jul. 17, 2003

Related U.S. Application Data

(60) Provisional application No. 60/332,868, filed on Nov. 12, 2001.

(51) Int. Cl.
*A61K 9/22* (2006.01)
(52) U.S. Cl. .................................... 424/468
(58) Field of Classification Search ............ 424/78.02, 424/468
See application file for complete search history.

(56) References Cited

U.S. PATENT DOCUMENTS

| | | | |
|---|---|---|---|
| 4,526,938 A | 7/1985 | Churchill et al. | |
| 4,942,035 A | 7/1990 | Churchill et al. | |
| 5,330,768 A | 7/1994 | Park et al. | |
| 5,709,852 A | 1/1998 | Gopalkrishnan et al. | |
| 5,869,103 A | 2/1999 | Yeh et al. | |
| 5,980,948 A | 11/1999 | Goedemoed et al. | |
| 6,117,949 A | 9/2000 | Rathi et al. | |
| 6,201,072 B1 | 3/2001 | Rathi et al. | |
| 6,296,842 B1 * | 10/2001 | Jaworowicz et al. | 424/78.02 |

FOREIGN PATENT DOCUMENTS

| | | |
|---|---|---|
| CA | 2214889 | 9/1996 |
| EP | 0 601 799 A1 | 6/1994 |
| WO | WO 93/25583 | 12/1993 |
| WO | WO 95/35097 | 12/1995 |
| WO | WO 01/41735 | 6/2001 |

OTHER PUBLICATIONS

Cho, K.Y., et al., "Protein release microparticles based on the blend of poly(D,L-lactic-co-glycolic acid) and oligo-ethylene glycol grafted poly(L-lactide)," *Journal of Controlled Release*, 76:275-284, (2001).

Lee and Kimura, "Synthesis and properties of poly(L-lactide) including polyether segments," *Kobunshi Ronbun.*, 52(11):692-697, (1995).

Bittner, B., et al., "Degradation and protein release properties of microspheres prepared from biodegradable poly(lactide-co-glycolide) and ABA triblock copolymers: influence of buffer media on polymer erosion and bovine serum albumin release," *Journal of Controlled Release*, 5(60):297-309, (1999).

Bezemer, J.M., et al., "Control of protein delivery from amphiphilic poly(ether ester) multiblock copolymers by varying their water content using emulsification techniques," *Journal of Controlled Release*, 66:307-320, (2000).

Morlock, Michael., et al., "Erythropoietin loaded microspheres prepared from biodegradable LPLG-PEO-LPLG triblock copolymers: protein stabilization and in-vitro release properties," *Journal of Controlled Release*, 56:105-115 (1998).

* cited by examiner

*Primary Examiner*—Sharon E. Kennedy
(74) *Attorney, Agent, or Firm*—Hamilton, Brook, Smith & Reynolds, P.C.

(57) ABSTRACT

The present invention relates to a novel series of polymers which have been prepared by blending hydrophobic biocompatible, biodegradable polymers or copolymers, such as poly(lactide-co-glycolide), and a biocompatible, amphipathic copolymer having a water absorption ratio of about 2 or less. A process for the preparation of the novel polymer blends and sustained release compositions comprising the novel polymer blends are also part of the invention described herein. Further the sustained release compositions can be used to deliver a biologically active with a desirable release profile and in a sustained fashion to a patient in need thereof.

43 Claims, 9 Drawing Sheets

BIOCOMPATIBLE POLYMER BLENDS AND USES THEREOF

RELATED APPLICATION

This application claims the benefit of U.S. Provisional Application No. 60/332,868, filed on Nov. 12, 2001. The entire teachings of the above application are hereby incorporated by reference.

BACKGROUND OF THE INVENTION

The PLG or poly(lactide-co-glycolide) family of polymers has traditionally been the polymer of choice for drug delivery systems. However, PLG can in some instances generate a pH drop within the polymer matrix, which can be deleterious to the incorporated agent, particularly when the agent is a labile agent such as a protein, polypeptide or oligonucleotide. In addition, the hydrophobic nature of PLG can result in problems with release of the incorporated agent due to adsorption of the agent onto the polymer surface, denaturation of the agent and aggregation of the agent. As such, new polymer compositions which can reduce the problems often encountered during processing of and release in vivo from polymeric sustained release compositions are needed.

SUMMARY OF THE INVENTION

The present invention is based upon the surprising discovery that the use of certain polymer blends (also referred to herein as, blend polymers) as the matrix for sustained release compositions can result in an improved sustained release composition showing one or more of the following: an increase in the duration of release of biologically active agent from the polymer matrix, a reduction in the initial release of active agent, an increased amount of active released and increased sustained levels of release of active agent. The polymer blend which provides the matrix for the sustained release composition comprise a hydrophobic biocompatible, biodegradable polymer and a biocompatible amphipathic polymer having a water absorption ratio of about 2 or less. Thus the sustained release compositions comprises the polymer blend and an active agent incorporated therein.

Accordingly, the present invention relates to a novel series of polymers which have been prepared by blending hydrophobic, biocompatible, biodegradable polymers or copolymers, such as poly(lactide-co-glycolide), and a biocompatible, amphipathic copolymer having a water absorption ratio of about 2 or less. A process for the preparation of the novel polymer blends and sustained release compositions comprising the novel blend polymers are also part of the invention described herein. Further the sustained release compositions can be used to deliver a biologically active agent with a desirable release profile and in a sustained fashion to a patient in need thereof.

More specifically, the sustained release composition of the invention comprises a biologically active agent incorporated in a polymer blend comprising a hydrophobic biocompatible, biodegradable polymer and a biocompatible amphipathic polymer having a water absorption ratio of about 2 or less. The amount of hydrophobic biocompatible, biodegradable polymer present in the polymer blend can range from about 10% w/w to about 90% w/w of the total weight of the polymer blend such as from about 20% to about 80%. The amount of amphipathic polymer having a water absorption ratio of about 2 or less which is present in the polymer blend can range from about 10% w/w to about 90% w/w of the total weight of the blend polymer, such as from about 20% to about 80% w/w.

The invention further relates to a method of delivering an active agent in a sustained fashion to a patient in need thereof comprising administering a therapeutically effective amount of a sustained release composition comprising a biologically active agent incorporated within a polymer blend comprising a hydrophobic biocompatible, biodegradable polymer and an amphipathic polymer having a water absorption ratio of about 2 or less.

The polymer blends of the present invention comprise a hydrophobic biocompatible, biodegradable polymer and a amphipathic polymer having a water absorption ratio of about 2 or less.

The amount of hydrophobic biocompatible, biodegradable polymer present in the polymer blend can range from about 10% w/w to about 90% w/w of the total weight of the polymer blend such as from about 20% to about 80%. The amount of amphipathic copolymer having a water absorption ratio of about 2 or less which is present in the polymer blend can range from about 10% w/w to about 90% w/w of the total weight of the polymer blend, such as from about 20% to about 80% w/w.

Figure 1:
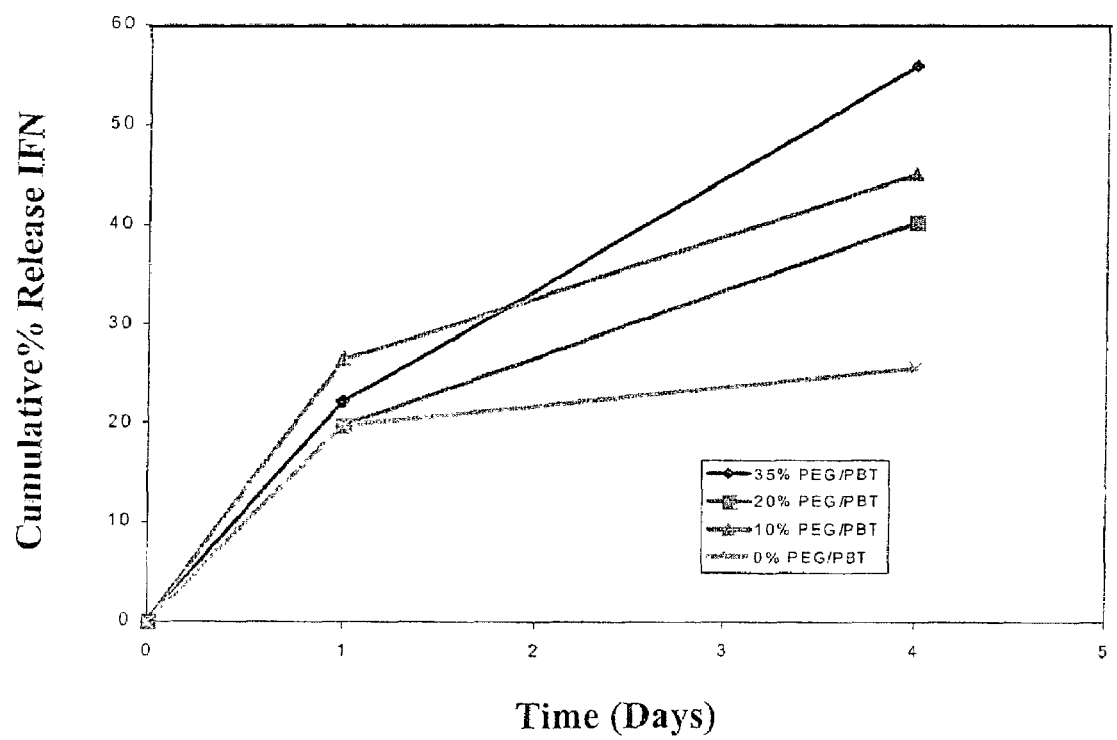
FIG. 1 is a graph of cumulative % release versus time in days for in vitro release testing over a four day period of IFN-containing microparticles prepared using polymer blends of 1000PEG70PBT30 and 5050 2A PLG and having a PEG/PBT:2A ratio of 35:65, 20:80, 10:90 and 0:100.

The foregoing and other objects, features and advantages of the invention will be apparent from the following more particular description of preferred embodiments of the invention.

DETAILED DESCRIPTION OF THE INVENTION

A description of preferred embodiments of the invention follows.

"Polymer blend" as that term is used herein, refers to a blend of two or more polymers and specifically a blend comprising a blend of a hydrophobic biocompatible, biodegradable polymer or copolymer, such as poly(lactide-co-glycolide), and a biocompatible, amphipathic polymer having a water absorption ratio of about 2 or less such as a PEG/PBT copolymer.

"Amphipathic polymer" as that term is used herein is any polymer which has both hydrophilic and hydrophobic subunits. The term "subunit" as used herein, refers to a portion of the polymer which includes multiple contiguous monomeric units (e.g., greater that about 10). The amphipathic polymers suitable for use in the present invention have a water absorption ratio of about 2 or less.

Examples of amphipathic polymers suitable for use in the invention include polyetherester copolymers such as PEG (polyethylene glycol)/PBT polylbutylene terephthalate) copolymers. Such copolymers are available from IsoTis, Inc. of the Netherlands and are described in U.S. Pat. No. 5,980,948 issued on Nov. 9, 1999 to Goedemoed et al., the entire contents of which are hereby incorporated by reference. The polymers are commonly referred to as a POLYACTIVE®. The POLYACTIVE® are synthesized in a two-step melt polycondensation procedure. The copolymers are abbreviated as aPEGbPBTc, in which a is the PEG molecular weight, b the weight % PEG-terephthalate and c the weight % PBT. A terephthalate moiety connects the polyethylene glycol units to the polybutylene terepthalate units of the copolymer, and thus such copolymers can also be referred to as a polyethylene glycol terephthalate/polybutylene terephthalate copolymer, or PEGT/PBT copolymer. Examples of this type of amphipathic polymer include, but are not limited to: 300PEGT80PBT20, 300PEGT70PBT30, 300PEGT55PBT45, 600PEGT80PBT20, 1000PEGT60PBT40, 1000PEGT70PBT30, 1000PEGT80PBT20.

Other amphipathic polymers suitable for use in the invention include block copolymers of a biocompatible hydrophobic polymer(A) and a biocompatible hydrophilic polymer (B). The biocompatible hydrophobic polymer (A) of the block amphipathic polymer can be the same or different from the hydrophobic biocompatible, biodegradable polymer of the blend polymer. In a preferred embodiment, the hydrophobic biocompatible polymer of the block polymer and of the blend polymer are the same. The block polymer can be a linear block copolymer of the formula A-B-A. Block copolymers of this type are described in detail in U.S. Pat. No. 4,526,938 issued on Jul. 2, 1985 to Churchill et al., the entire contents of which are hereby incorporated by reference. The class of nonionic polymer surfactants referred to as poloxamers are suitable for use as the hydrophilic polymer B. Poloxamers are themselves block copolymers of polyethyleneoxide (PEO) and polypropylencoxide (PPO) commonly referred to as PLURONIC™ polymers. The general structure for poloxamers is $HO(CH_2CH_2O)_a(CH(CH_3)CH_2O)_b(CH_2CH_2O)_cH$ where b is at least 15 and $(CH_2CH_2O)$ a+c is varied from 20 to 90% by weight. The poly(oxypropylene) segment is hydrophobic; the poly(oxyethylene) segment is hydrophilic. Molecular weights of the poloxamers can range from 1000 to greater than 16,000.

Examples of specific poloxamers include poloxamer 407 sold under the trademark PLURONIC F127, poloxamer 188 sold under the trademark PLURONIC F68 (available from BASF Wyandotte).

(PEO/PPO/PEO) block copolymers exhibit a wide range of hydrophilicity/hydrophobicity as a function of PEO/PPO ratio. The PLURONIC™ containing block copolymers which are preferred for use in the polymer blends of this invention have a water absorption ratio of about 2 or less determined as described herein.

Suitable hydrophobic biocompatible polymers, for use in the amphipathic triblock polymer can be either biodegradable or non-biodegradable polymers or blends or copolymers thereof. In a preferred embodiment, the hydrophobic biocompatible polymers are biodegradable.

As used herein, a polymer is biocompatible if the polymer and any degradation products of the polymer are generally non-toxic to the recipient and also possess no significant deleterious or untoward effects on the recipient's body, such as a significant immunological reaction at the injection site.

"Biodegradable", as defined herein, means the composition will degrade or erode in vivo to form smaller chemical species. Degradation can result, for example, by enzymatic, chemical and physical processes.

Suitable hydrophobic biocompatible, biodegradable polymers include, for example, poly(lactides), poly(glycolides), poly(lactide-co-glycolides), poly(lactic acid)s, poly(glycolic acid)s (all of which can be referred to as PLG as defined below), polycarbonates, polyesteramides, polyanhydrides, polyorthoesters, poly(dioxanone)s, polycaprolactones, biodegradable polyurethane, polycyanoacrylates blends thereof, and copolymers thereof. These polymers can be used as the hydrophobic biocompatible, biodegradable polymer of the blend polymer and can also be the hydrophobic, biocompatible polymer of the amphipathic triblock polymers described above.

Hydrophobic biocompatible, non-biodegradable polymers suitable for use in the amphipathic triblock polymers of the invention, include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polypropylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the hydrophobic, biocompatible, biodegradable polymer of the polymer blend is a PLG polymer. The term PLG as used herein is intended to refer to a polymer of lactic acid alone, a polymer of glycolic acid alone, a mixture of such polymers, a copolymer of glycolic acid and lactic acid, a mixture of such copolymers, or a mixture of such polymers and copolymers. Preferably, the PLG is a poly(lactide-co-glycolide). The end group of the polymer can be a carboxylic acid, and alkyl ester or mixtures of polymer with different end groups. The poly(lactide-co-glycolide) can have a lactide:glycolide ratio, for example, of about 10:90, 25:75, 50:50, 75:25 or 90:10 and a molecular weight of about 5,000 Daltons to about 150,000 Daltons.

In another embodiment, the hydrophobic, biocompatible polymer of the amphipathic polymer is a biodegradable PLG polymer, such as a poly(lactide-co-glycolide).

In a further embodiment, the hydrophobic biocompatible, biodegradable polymer of the polymer blend and the hydrophobic, biocompatible portion of the amphipathic triblock polymer are the same.

The sustained release composition of the invention comprises a biologically active agent incorporated in a polymer blend comprising a hydrophobic biocompatible, biodegradable polymer and a biocompatible amphipathic polymer having a water absorption ratio of about 2 or less.

The amount of hydrophobic biocompatible, biodegradable polymer present in the blend polymer can range from about 10% w/w to about 90% w/w of the total weight of the polymer blend such as from about 20% to about 80%.

The amount of amphipathic polymer having a water absorption ratio of about 2 or less which is present in the polymer blend can range from about 10% w/w to about 90%w/w of the total weight of the polymer blend, such as from about 20% to about 80% w/w.

In particular embodiments, when the amphipathic copolymer is a polyetherester copolymer, such as a polyethylene glycol terephthalate/polybutylene terephthalate (PEG/PBT) having a water absorption ratio of about 2 or less, the amount of the amphipathic copolymer present in the blend is preferably from about 10% w/w to about 50% w/w, such as from about 20% to about 40% of the total weight of the polymer blend or from about 30% to about 40%.

In other embodiments, when the amphipathic copolymer is a triblock of PLG-poloxamer-PLG having a water absorption ratio of about 2 or less, the amount of the amphipathic copolymer present in the blend is preferably from about 50% w/w to about 90% w/w, such as from about 60 w/w to about 80% w/w of the total weight of the polymer blend.

"Water absorption ratio" as that term is used herein, refers to the ratio of the weight of a polymer following incubation in an aqueous buffer solution at physiologic temperature and pH for a sufficient amount of time needed to reach equilibrium (i.e., the point at which a maximum amount of water has been absorbed, generally about 2 to 3 days) divided by the weight of the polymer prior to incubation.

"Copolymer" as that term is used herein is any polymer which has two or more different repeat units or monomers such as random copolymers, alternating copolymers, block copolymers and graft copolymers. As such, the term copolymer includes therefore the PEG/PBT copolymers as well as the triblock polymers such as PLG-F127-PLG.

"Patient" as that term is used herein refers to the recipient of the treatment. Mammalian and non-mammalian patients are included. In a specific embodiment, the patient is a mammal, such as a human, canine, murine, feline, bovine, ovine, swine or caprine. In a preferred embodiment, the patient is a human.

The term "sustained release composition" as defined herein, comprises a blend polymer comprising a hydrophobic biocompatible, biodegradable polymer and an amphipathic polymer with a water absorption ratio of 2 or less having incorporated therein at least one biologically active agent.

Typically, the sustained release composition can contain from about 0.01% (w/w) to about 50% (w/w) of the biologically active agent (dry weight of composition). The amount of agent used will vary depending upon the desired effect of the agent, the planned release levels, and the time span over which the agent will be released. A preferred range of agent loading is between about 0.1% (w/w) to about 30% (w/w) agent. A more preferred range of agent loading is between about 0.5% (w/w) to about 20% (w/w) agent.

The sustained release compositions of this invention can be formed into many shapes such as a film, a pellet, a rod, a filament, a cylinder, a disc, a wafer, nanoparticles or a microparticle. A microparticle is preferred. A "microparticle" as defined herein, comprises a blend polymer component having a diameter of less than about one millimeter and having a biologically active agent dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of biologically active agent is a release of the agent from a sustained release composition. The release occurs over a period which is longer than that period during which a therapeutically significant amount of the biologically active agent would be available following direct administration of a solution of the biologically active agent. It is preferred that a sustained release be a release of biologically active agent which occurs over a period of greater than two days such as about one week, about two weeks, about three weeks or more. A sustained release of biologically active agent, from a sustained release composition can be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

As used herein, the term "a" or "an" refers to one or more.

As used herein, a "therapeutically effective amount", "prophylactically effective amount" or "diagnostically effective amount" is the amount of the sustained release composition needed to elicit the desired biological response following administration.

The term "biologically active agent," as used herein, is an agent, or its pharmaceutically acceptable salt, which when released in vivo, possesses the desired biological activity, for example therapeutic, diagnostic and/or prophylactic properties in vivo. It is understood that the term includes stabilized biologically active agents as described herein.

Examples of suitable biologically active agents include proteins such as immunoglobulins, antibodies, cytokines (e.g., lymphokines, monokines, chemokines), interleukins, interferons, erythropoietin, nucleases, tumor necrosis factor, colony stimulating factors, insulin, enzymes (e.g. superoxide dismutase, plasminogen activator, etc.), tumor suppressors, blood proteins, hormones and hormone analogs (e.g., growth hormone, adrenocorticotropic hormone, and luteinizing hormone releasing hormone (LHRH)), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and sodium heparin; hemostatic agents such as thrombin, menadione sodium bisulfite and acetomenaphthone; antituberculous agents such as isoniazide and ethanbutol; hormones such as prednisolone sodium phosphate and methimazole; antipsychotic agents such as risperidone; and narcotic antagonists such as nalorphine hydrochloride.

In one embodiment, the biologically active agent is stabilized. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. The stabilizing agent can be present in the mixture. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent applications Ser. No. 08/934,830 to Burke et al., filed on Sep. 22, 1997 and Ser. No. 09/104,549 to Burke, filed on Jun. 25, 1998 the entire teachings of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. It is preferred that the metal cation be complexed to the biologically active agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and HPLC analysis on particles of metal cation-stabilized biologically active agents prior to and following particle size reduction and/or encapsulation. The molar ratio of metal cation to biologically active agent is typically between about 1:2 and about 100:1, preferably between about 2:1 and about 12:1.

Examples of stabilizing metal cations include, but are not limited to, $K^+$, $Zn^{+2}$, $Mg^{+2}$ and $Ca^{+2}$. Stabilizing metal cations also include cations of transition metals, such as $Cu^{+2}$. Combinations of metal cations can also be employed.

The biologically active agent can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

Further, excipients can be added to maintain the potency of the biologically active agent over the duration of release and modify polymer degradation. The excipients can be added to the dispersed system which is then atomized or can be added to the mixture which is subjected to fragmenting either before or after fragmentation of the dried substance to achieve particles of biologically active agent. Suitable excipients include, for example, carbohydrates, amino acids, fatty acids, surfactants, and bulking agents, and are known to those skilled in the art. An acidic or a basic excipient is also suitable. The amount of excipient used is based on ratio to the biologically active agent, on a weight basis. For amino acids, fatty acids and carbohydrates, such as sucrose, trehalose, lactose, mannitol, dextran and heparin, the ratio of carbohydrate to biologically active agent, is typically between about 1:10 and about 20:1. For surfactants the ratio of surfactant to biologically active agent is typically between about 1:1000 and about 2:1. Bulking agents typically comprise inert materials. Suitable bulking agents are known to those skilled in the art.

The excipient can also be a metal cation component which is separately dispersed within the polymer matrix. This metal cation component acts to modulate the release of the biologically active agent and is not complexed with the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3.Mg(OH)_2.5H_2O$), $MgSO_4$, $Zn(OAc)_2$, $Mg(OAc)_2$, $ZnCO_3$ (such as $3Zn(OH)_2$ $2ZnCO_3$)$ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is firther described in U.S. Pat. No. 5,656,297 to Bernstein et al. and co-pending U.S. patent application Ser. No. 09/056,566 filed on Apr. 7, 1998, the teachings of both of which are incorporated herein by reference in their entirety.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

The composition of this invention can be administered in vivo, for example, to a human, or to an animal, orally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of biologically active agent based on the known parameters for treatment with the particular agent of the various medical conditions.

Therapeutic uses of the sustained release compositions of the present invention depend on the biologically active agent which is incorporated into the blend polymer. One skilled in the art will readily be able to adapt a desired biologically active agent to the present invention for its intended therapeutic uses. Therapeutic uses for such agents are set forth in greater detail in the following publications hereby incorporated by reference in their entirety. As such, therapeutic uses include but are not limited to, uses for protein such as interferons (See, U.S. Pat. Nos. 5,980,884 and 5,372,808), interleukins (See, U.S. Pat. No. 5,075,222), erythropoietins (See, U.S. Pat. Nos. 4,703,008, 5,441,868, 5,618,698, 5,547,933 and 5,621,080), and granulocyte-colony stimulating factors (See, U.S. Pat. Nos. 4,999,291, 5,581,476, 5,582,823, 4,810,643 and PCT Publication WO 94/7185). In addition, the present sustained release compositions may also be used for the manufacture of one or more medicaments for the treatment or amelioration of the conditions the biologically active agent incorporated therein is intended to treat.

EXEMPLIFICATIONS

POLYMER 2A: Available from Alkermes, Inc. Cincinnati, Ohio, Cat. No.: 5050DL2A Poly (lactide-co-glycolide); 50:50 lactide: glycolide ratio; 10 kD Mol. Wt.; acid end group.

POLYMER 2.5A: Cat. No. 5050 DL2.5A, Poly(lactide-co-glycolide); 50:50 lactide:glycolide; 20 kD Mol. St., acid end group.

POLYMER 2M: Cat. No. 5050 DL2M Poly(lactide-co-glycolide); 50:50 lactide:glycolide ratio; 16 kD Mol.Wt., methyl ester end group.

General Prolease® Process for Preparing Microparticles

FORMATION of a polymer solution by dissolving polymer blend in a suitable polymer solvent.

ADDITION of the active agent to the polymer blend solution to form a polymer/active agent mixture.

OPTIONAL homogenization of the polymer/active agent mixture.

ATOMIZATION of the polymer/active agent mixture by sonication, and freezing of the droplets by contact with liquid nitrogen.

EXTRACTION of the polymer solvent from the polymer/active agent droplets into an extraction solvent (e.g., −80° C. ethanol), thereby forming particles comprising a polymer/active agent matrix.

ISOLATION of the particles from the extraction solvent by filtration.

REMOVAL of remaining solvent by evaporation.

SIEVING of particles by passage through an appropriately sized mesh so as to produce an injectable product.

Example 1

PEG/PBT Blends

Experimental Methods

Various compositions of the polyetherester copolymers having a PEG (polyethylene glycol)/PBT polylbutylene terephthalate) polymer, available from IsoTis, Inc. of the Netherlands and referred to as a POLYACTIVE®, was assessed prior to preparation of the polymer blends of the invention comprising the PEG/PBT.

The copolymers are abbreviated as aPEGbPBTc, in which a is the PEG molecular weight, b the weight % PEG-terephthalate and c the weight % PBT. The copolymers which were assessed are listed in Table 1. In some instances the polymers are referred to as aPEGTbPBTc.

Characterization of the PEG/PBT Polymers

Solubility Studies

Polymer solutions of the PEG/PBT copolymers of Table 1 were prepared using various solvents to test for solubility. The polymer solutions were then transferred into chilled ethanol to determine the degree of insolubility. Further details and results of the solubility studies are described in detail below.

Ten percent polymer solutions were made using all of the above compositions in methylene chloride. All compositions swelled significantly but were eventually soluble in the $MeCl_2$, though the compositions containing the highest molecular weight PEG (4000PEGT80PBT20) or highest ratio of PBT to PEG (55:45 and 60:40) took the longest to solubilize.

The polymer solutions were then poured into −80° C. ethanol to determine solubility. In all cases, the polymer precipitated out of solution, indicating lack of solubility in ethanol. Alternate cure solvents were also tested with select copolymer compositions, including heptane/ethanol combinations, mixed hexanes, and a mixed hexanes/ethanol combination. The copolymers were determined to be sufficiently insoluble in all tested solvents.

Intrinsic Viscosity and Swelling

The intrinsic viscosity (IV) as determined in $CHCl_3$ at 25° C. and the swelling (determined as wet weight/dry weight in accordance with methods described in U.S. Pat. No. 5,980,948 to Goedemoed et al.) were determined for the copolymer samples. The information is set forth in Table 1. Water absorption ratio as that term is used herein is the same as the value for "swelling" set forth in Table 1.

Specifically, dry films (15 mm in diameter and 50-100 μm in thickness) were weighed and immersed in PBS at 37° C. in a shaking bath. The equilibrium volume swelling ratio Q was determined from the equilibrium weight of the swollen samples using a density of 1.2 g/mL for all polymers. Prior to measuring the weight, surface water was removed by blotting the surface with a tissue. Equilibrium swelling was reached within three days.

TABLE 1

PEG/PBT IV/SWELLING/MASS LOSS DATA

| Composition | Intrinsic Viscosity | Swelling | Mass Loss (%) |
|---|---|---|---|
| | | | At Day 56 |
| 300PEGT80PBT20 | ND | <1.1 | 0.0 |
| 300PEGT70PBT30 | 0.479-0.484 | <1.1 | 2.7 |
| 300PEGT55PBT45 | 0.598-0.610 | <1.1 | 2.8 |
| 600PEGT80PBT20 | 0.75-0.79 | 1.55 | 23.9 |
| 1000PEGT60PBT40 | ND | 1.6 | 10.6 |
| 1000PEGT70PBT30 | 0.767-0.794 | 1.8 | 11.7 |
| 1000PEGT80PBT20 | 0.695-0.699 | 2.0 | 28.6 |
| 2000PEGT80PBT20 | 1.00-0.97 | ND (2-3) | 20.7 |
| 3000PEGT80PBT20 | 0.877-0.884 | ND (2-3) | 30.3 |
| 4000PEGT80PBT20 | ND | 3.2 | 18.9 |

In Vitro Degradation of PEG/PBT Copolymers

About 50 mg of each polymer composition was loaded into a Carver® test cylinder outfit and placed at 65° C. The test cylinder outfit was removed from the oven and the polymer was pressed into a pellet using the Carver® manual hydraulic press under 4000 lbs. of pressure for 5 minutes. Pellets were weighed and placed into 20-mL scintillation vials. 5 mL of 50 mM HEPES buffer with 10 mM KCl and 0.1% sodium azide (pH-7.2) was added to each vial, and vials were placed at 37° C. for incubation. Pellets were removed at days 7, 21, 29, 44, and 56. Supernatant was aspirated off the pellet and wet pellets were dried and reweighed. The profiles of polymer degradation are described below.

Mass loss from pellets of the pure PEG/PBT copolymers varied with composition over the 8 weeks of the study, with the more hydrophobic polymers showing the slowest degradation. Polymers made from a PEG with a 300 Dalton molecular weight had the lowest mass loss of only 1-3% at the last timepoint. Next are the 1000PEG60PBT40 and the 1000PEG70PBT30, which both lost around 10-12% of their mass over 56 days. Those polymers consisting of 80% PEG and 20% PBT lost between 19% and 30% of their initial pellet mass, although within this group there was no correlation between PEG molecular weight and the degree of mass loss. In general, the mass loss did not increase between 4 and 8 weeks, to the degree that any trend could be discerned given the experimental error present in these experiments. The variation in pellet structure, due to the physical properties of PEG/PBT copolymers, in some instances led to loss of pellet mass during removal of buffer or removal of the pellet from the vial. The results are set forth in Table 1 above.

Initial degradation studies on some of the polymer blends between poly(lactide-co-glycolide) and thePEG/PBT copolymers containing PEG units with molecular weights of 2000 or more were also carried out. Pellets with 50% of the initial weight consisting of 5050 2.5A exhibited about 43-48% mass loss over 8 weeks, whereas those compositions containing 25% PLG lost about 30-35% of their initial mass in the same time. There were not significant differences between the various PEB/PBT copolymers. The degree of mass loss at 3 weeks was around 20% for most of the compositions, so there was increased degradation over time in the blends. For comparison, erosion of the PLG alone was about 50% at 3 weeks, and nearly complete at the end of four weeks.

Example 2

Microparticle Preparation

Microparticle compositions were prepared from polymer blends of poly(lactide-co-glycolide) and various PEG/PBT copolymers of Table 1. The microparticles were prepared using the general PROLEASE™ process outlined above.

Figure 2:
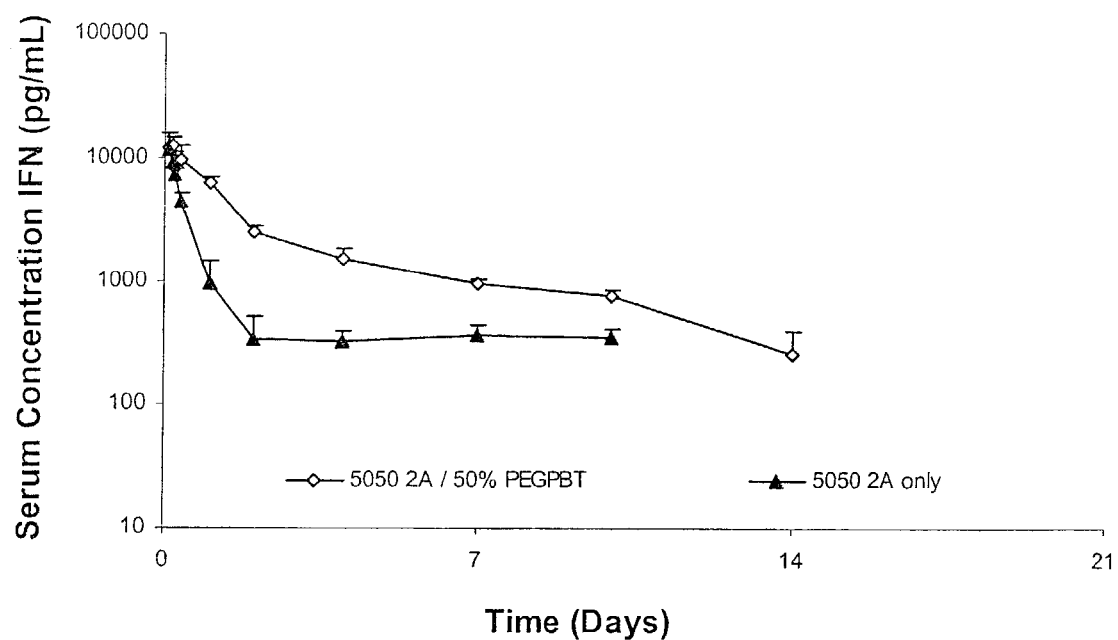
FIG. 2 is a graph of IFN serum concentration in rats versus time in days following administration of the indicated formulation.

Selected PEG/PBT (1000PEGT70PBT30, 1000PEGT60PBT40, 1000PEG80PBT20, 2000PEGT70PBT30 4000PEG80PBT20) polymers were blended with poly(lactide-co-glycolide) in the varying ratios: such as 10:90, 20:80, 35:65, 50:50 75:25 PEG/PBT to poly(lactide-co-glycolide). Blending is done on a weight to weight ratio of the selected polymers. For each of the blend polymer compositions, a 5% or 6% polymer solution (750 or 900 mg of each polymer in 15 mL $MeCl_2$) was prepared in methylene chloride. A predetermined amount of the selected biologically active agent and any excipients desired were then added to the polymer solution. The polymer solution (either with or without active (blanks)) was then sprayed. The flow rate of the solution during spraying was about 2 mL/min. The droplets resulting from spraying of the polymer solution were cured using either a mixture of heptane/ethanol (~35% heptane) or 100% mixed hexanes as the cure solvent.

α-IFN-Containing Microparticles

Microparticles containing α-IFN were prepared with a 1.4-2.0% target load of protein, with 5% magnesium carbonate or magnesium hydroxide co-encapsulated with a α-IFN lyophilized powder (Spray frozen, lyophilized protein powder containing zinc-complexed α-IFN, sucrose (1:1 ratio to the IFN), zinc acetate and Tris buffer (42% IFN by weight).

In one preparation, the polymer phase employed to produce the IFN-containing microparticles was about 50% 1000PEG70PBT30 copolymer blended with Medisorb 5050 2A as the PLG. Two other PEG/PBT copolymers (1000PEG60PBT40 and 4000PEG80PBT20) were also blended with the PLG in αIFN-loaded microspheres.

In other preparations, the amount of 1000PEG70PBT 30 was 0%, 10%, 20% or 35% with the remainder 5050 2A PLG.

In Vitro Release

In vitro release studies were carried out on various batches of α-IFN loaded microparticles. Approximately 20 mg of microparticles was weighed out into microcentrifuge tubes in duplicate for each microparticles formulation. 300 μL of buffer (25 mM Phosphate, 130 mM NaCl, and 0.3 mM EDTA at pH=7.2) was added to each microcentrifuge tube. Samples were vortexed for about 2 seconds to suspend the microparticles, then tubes were placed on a rocker at 37° C. overnight. After 24 hours, supernatants were collected from each tube, centrifuged at 14,000 rpm for 6 minutes using the Centrifuge 5415C to separate out any remaining particulates, the supernatant was transferred to another tube. Fresh buffer was added to continue the assay out to 4 days. Protein concentration in each sample was measured using a BioRad Protein Assay.

FIG. 1 graphs the results of in vitro release testing over a four day period obtained for αIFN-containing microparticles prepared as described above for polymer blends using 1000PEG70PBT30 and 5050 2A PLG and having a PEG/PBT:2A ratio of 35:65, 20:80, 10:90 and 0:100. The increase in PEG/PBT content correlates well with the increase in cumulative % αIFN release. For example, the addition of 35% PEG/PBT to the PLG brings the % released up from 20% to about 50% in four days.

In Vivo Studies

In vivo pharmacokinetic studies were performed with microparticles made with various PEGT/PBT:PLG formulations and loaded with α-IFN. The α-IFN-containing microparticles prepared as described above were tested in vivo as follows. Male Sprague-Dawley rats weighing approximately 450±50 grams (3 animals per group) were treated with 5 mg/kg Sandimmune Cyclosporine IP daily for days 0-14 post injection (except Sundays). The desired dose of microparticles in vehicle were injected into the interscapular region of the animals using a 1.0 cc syringe and a 21 gauge needle. The dose of microparticles was about 17 mg of microparticles suspended in 1.0 mL of a vehicle comprising 3.0% carboxymethyl cellulose (CMC), 0.9% NaCl, 0.1% Tween 20.

Blood samples were taken at 2, 4, 6, 9 and 24 hours and 2, 4, 7, 10, 14, 17, 21, 24 and 28 days. For some animals it was not possible to collect blood samples for every time point desired. The serum was separated and IFN concentration determined using ELISA.

The Interferon alpha ELISA (Endogen, Inc.) is an enzymatically amplified "two step" sandwich-type immunoassay. In the assay, standards, controls and unknown rat serum samples are incubated in microtitration wells that have been coated with anti-human IFNα capture antibody. After incubation and washing, the wells are treated with another anti-human IFNα detection antibody labeled with the enzyme horseradish peroxidase (HRP). After a second incubation and washing step, the wells are incubated with the substrate tetramethylbenzidine (TMB). An acid stopping solution is then added and degree of enzymatic turnover of the substrate is determined by dual wavelength absorbance measurement at 450 nm and 620 nm. The absorbance measured is directly proportional to the concentration of IFNα present. A set of IFNα standards is used to plot a standard curve of absorbance versus IFNα concentration. Using a four parameter fit standard curve, the IFNα concentration in the unknowns can be calculated.

Specifically, the initial in vivo study with α-IFN employed a microparticle formulation having a 50:50 (w/w) blend of 1000PEG70PBT30:50502A PLG with 5% magnesium hydroxide and about a 1.4% load of α-IFN in the form of a zinc-complexed lyophilizate as described above with about a 6:1 to 10:1 molar ratio of Zn to α-IFN as described in U.S. Pat. No. 6,165,508. The results of this study is set forth in FIG. 2. The relative bioavailability achieved for the alpha-IFN in the blend microparticles was determined to be 99% as compared to the a subQ bolus injection compared to 25% for the PLGA alone microparticles as compared to the a subQ bolus injection.

Figure 3:
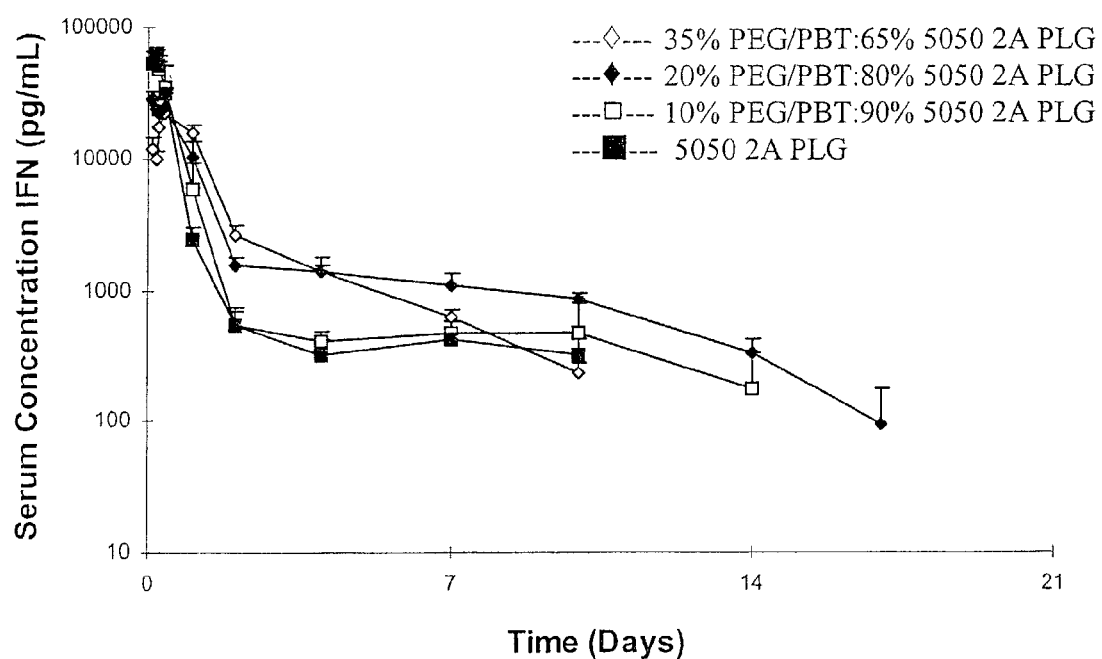
FIG. 3 is a graph of IFN serum concentration in rats versus time in days following administration of the indicated formulation.

In a subsequent study, the 1000PEGT70PBT30 and 2A PLG were blended at three w/w ratios. Specifically, blends of 35%, 20% and 10% 1000PEGT70PBT30 and the remainder 5050 2APLG were used to prepare microparticles having a target load of α-IFN of 1.4% as described above with 42% IFN and magnesium hydroxide at about 5% The microparticles were tested in vivo in accordance with the protocol set forth above. Results of this study are set forth in FIG. 3. The correspondence of the legends in FIG. 3 with specific microparticle formulations is as follows: 35% PEG/PBT, 20% PEG/PBT, 10% PEG/PBT and 5050 2A PLG alone.

Figure 4:
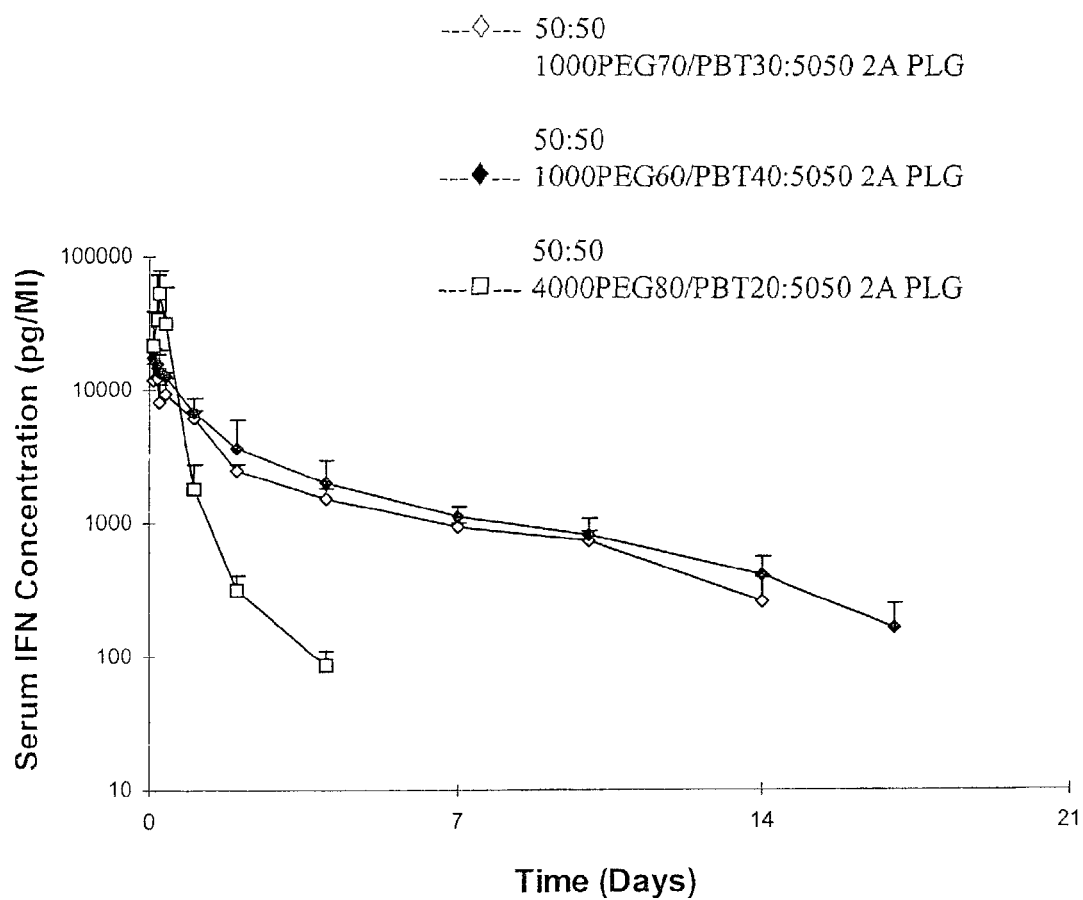
FIG. 4 is a graph of IFN serum concentration in rats versus time in days following administration of the indicated formulation.

Additional formulations of α-IFN microparticles was prepared having a 50:50 w/w PEG/PBT:PLG ratio. Specifically, the blends were: 4000PEG80PBT20 and 5050 2A PLG; 1000PEG70PBT30 and 50502A PLG; and 1000PEG60PBT40 and 5050 2A PLG having a target load of α-IFN of 1.4% prepared as described above and magnesium hydroxide at about 5%. The microparticles were tested in vivo as described above. The results are presented graphically in FIG. 4. The correspondence of the legends in FIG. 4 and the specific microparticle formulation is as follows: 50:50 4000PEG80PBT20:5050 2A PLG; 50:50 100OPEG70PBT30:5050 2A PLG; and 50:50 1000PEG60PBT40:5050 2A PLG). It can be seen from FIG. 4, that use of a PEG/PBT with a high molecular weight, low PBT content and water absorption ratio greater than 2 results in a higher burst and shorter duration of release than microparticles prepared from blends where the water absorption ratio of the amphipathic polymer is about 2 or less.

Example 3

FSH-Containing Microparticles

FSH-containing microparticles were manufactured with an approximately 0.5% load of the protein, using a protein powder consisting of 80% sucrose, 10% FSH and 10% phosphate salts. Two batches were prepared with 20% of the polymer consisting of the 1000PEG70PBT30, and the remainder either 5050 2A or a blend of 5050 2M and 5050 2A (75:25 blend). The general PROLEASE™ procedure outlined above was employed. Ethanol was used as the cure solvent in this case.

In Vivo

The FSH-containing microparticles were analyzed in vivo for release profiles. The injected dose was nominally 20 mg of microparticles loaded with 0.5% load of FSH, or 100 μg protein. PK data are expressed as the data dose-normalized to a 200 μg/kg dose.

In a typical PK experiment, three male Sprague-Dawley rats (450±50 g) were injected subcutaneously with 20 mg of microparticles suspended in 0.175 mL of diluent having 3% carboxymethyl cellulose, 0.9% NaCl, and 0.1% TWEEN-20. Serum samples were collected for several time points for the first day, and once per day for up to 14 days. FSH was quantitated from serum samples using the MAIAclone (IRMA) provided by BioChem. Immunosystems Italia S.P.A. Data presented are typically dose-normalized to 200 micrograms FSH/kg.

Figure 5:
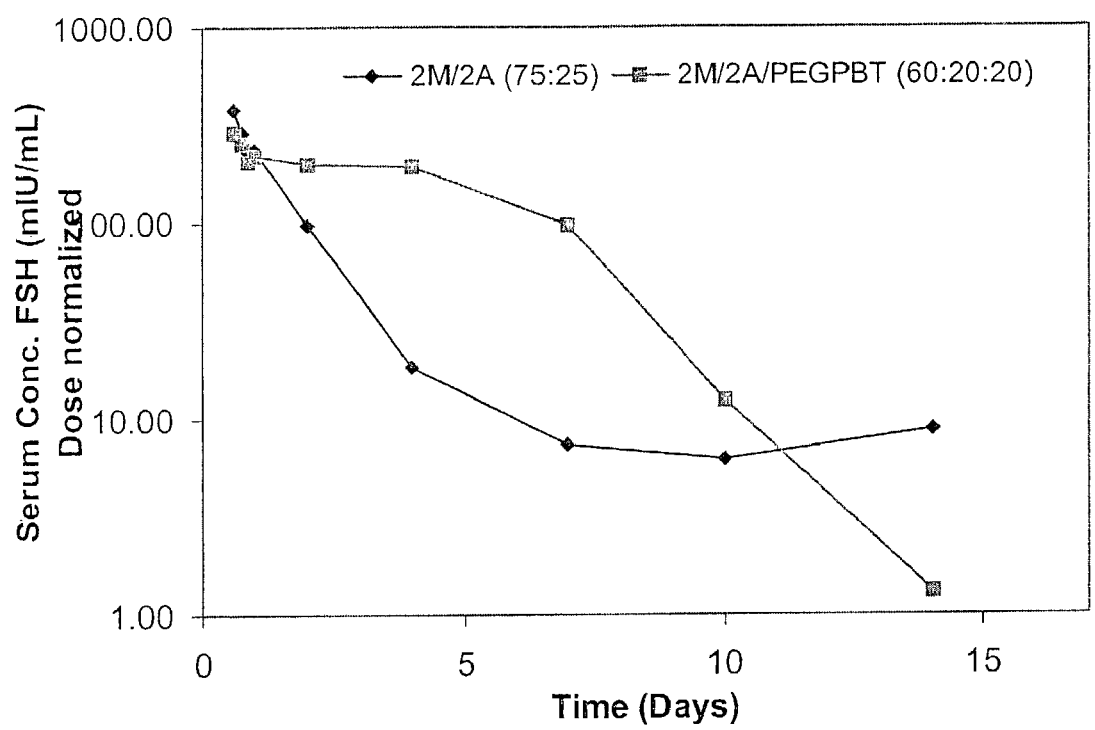
FIG. 5 is a graph of FSH serum concentration in rats versus time in days following administration of the indicated FSH-microparticle formulation.

The results of in vivo testing are set forth in FIG. 5. The graph in FIG. 5 shows an increase in bioavailability and sustained serum drug concentrations when the polymer 75:25 5050 2M:2A is blended with 20% PEG/PBT. That is, the results of in vivo testing set forth in FIG. 5 show an almost linear release profile over the first 7 days and serum concentrations an order of magnitude higher than the 2M/2A blend by itself between 2 and 7 days after dosing. Relative bioavailability was doubled from 30% to 65% as a result. When the blend polymer was the 5050 2A PLG and 20% 1000PEG70PBT30 the relative bioavailability was increased from 35% to 45%, with a substantially linear release profile as compared to the 5050 2A PLG alone.

Example 4

Triblock Blends

SUMMARY: PLG-Poloxamer-PLG Triblock polymers were prepared. The triblocks can be prepared by thermal condensation to achieve block copolymers with desirable copolymer composition and block lengths. The composition of the triblock polymer and relative block lengths can be confirmed using standard method of analysis such as $^1$H-NMR. The triblock polymers can also be prepared in a melt process which involves ring opening polymerization of the A block (e.g., PLG) using the B block (e.g., PLURONICS™) as the initiator. For example, the PLG-PLURONIC™-PLG triblock copolymer can be prepared by stannous octoate catalyzed ring-opening polymerization using the PLURONICS™ as the intiator. The mole ratio of PLURONICS™ to PLG is used to control the lengths of the PLG blocks and can provide a series of polymers with varying block contents. The synthesis of triblock polymers of this type can be found in WO 01/41735 and U.S. Pat. No. 4,942,035 to Churchill et al. the entire content of both of which is hereby incorporated by reference.

The triblock polymers were then blended with PLG to give a polymer blend comprising PLG and the triblock. The polymer blend was then used to prepare microparticles for sustained release of active agent. Specific agents which were encapsulated include alpha-interferon (α-IFN) and FSH. The methods for preparing the triblock polymer, the polymer blend of PLG and triblock and microparticles having the blend as the polymer matrix, are set forth below. In addition, the in vitro and in vivo data resulting from testing of the triblock, blend and microparticles prepared are also provided.

PLG-Poloxamer Triblock

The polymer is a triblock copolymer comprising 90% of 50:50 poly(dl-lactide-co-glycolide) and 10% of Poloxamer 407 (PLURONIC F-127™). The preparation of the triblock copolymers by ring opening polymerization of dl-lactide and glycolide initiated by reaction with Poloxamer is set forth below:

Briefly, dl-lactide 99.9+%, available from Purac and glycolide 99.9+% available from Purac were added into a reactor vessel equipped with stirrer and nitrogen inlet. After the monomers were completely melted, an amount of 0.2% of stannous octoate available from Sigma was added as catalyst, followed by addition of Poloxamer 407™ with a weight-average molecular weight of 9,840-14,600. Polymerization was carried out at 150° C. for 24 hours under nitrogen blanket. Vacuum was applied for 3 hours to remove the unreacted monomers.

Other triblocks that were synthesized include varying the lactide to glycolide ratios in the final triblock from 50:50 up to 90:10 lactide to glycolide, while keeping the F127 ratio at 10%, as well as varying the F127 poloxamer concentration in the final triblock from 10% up to 30%, with the remaining PLGA comprised of a 50:50 lactide to glycolide. These changes in ratios of either lactide to glycolide or F127 to PLGA were made by varying the input mass ratios of each prior to initiation of polymerization.

The resulting triblock copolymer had the following properties:
- Intrinsic Viscosity (IV) range of 0.5-0.7 dL/g and weight-average molecular weight of between 50,000 and 100,000.
- A-B-C-B-A blocks consisting of poly(dl-lactide-co-glycolide) as "A" end block, Polyethylene oxide as "B" block and Polypropylene as "C" block.
- The weight ratio of Poly(dl-lactide-co-glycolide) and Poloxamer is 90:10.
- The mole ratio of lactide and glycolide is about 53:47 by proton NMR.
- Good solubility in organic solvents including methylene chloride, chloroform, ethyl acetate, acetone.
- Water Absorption Ratio of 1.15.

The triblock polymer was then blended with PLG to achieve a blended polymer. Blending of the triblock and PLG was achieved by dissolving both polymers in methylene choride and then spray freeze drying with or without lyophilized drug substance.

In Vitro Degradation of Pellets: Determination of Water Absorption Ratio

Materials:
50 mM HEPES buffer, with 10 mM KCl, 0.1% Sodium Azide, pH 7.2
Alkermes 5050 DL 2A polymer
90:10 PLG/F127 triblock prepared as described above
Blend of 80% 90:10 PLG:F127 and 20% 2A prepared as described above Procedure:
For each pellet, about 160 mg of total polymer was loaded into a 9 mm i.d. Carver® test cylinder set and placed at 65° C. The test cylinder set was removed from the oven and the polymer was pressed into a pellet using the Carver® manual hydraulic press under 4000 lbs. of pressure for 5 minutes. Pellets were weighed and placed into 20-mL scintillation vials, then covered with 10 mL of the HEPES buffer and incubated at 37° C. Four pellets were prepared for each composition, using ground up polymer powder for both pure polymer compositions and blends.

After 48 hours of incubation, one pellet of each composition was removed from the buffer, patted dry on tissue, and then weighed to determine the water uptake of the pellet. Then this pellet was placed back in the same buffer and incubated at 37° C. until it was used for the Day 7 time point.

Figure 6:
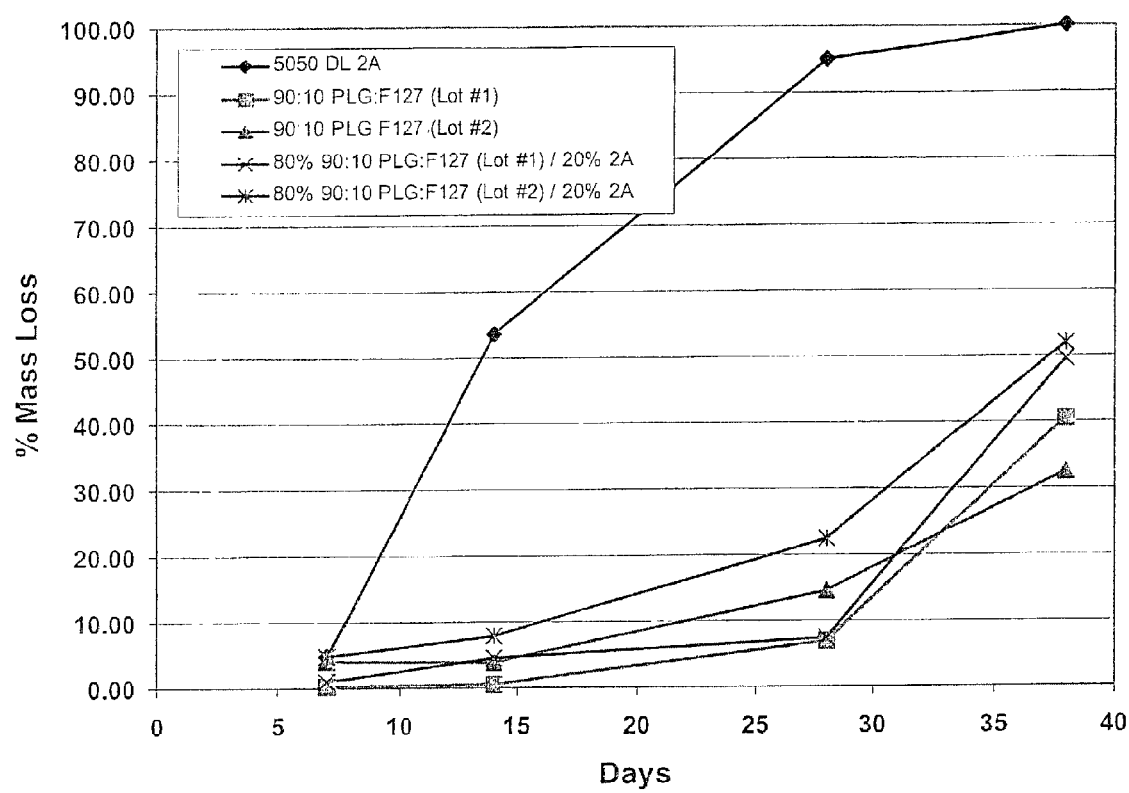
FIG. 6 is a graph of % Mass Loss versus time in days following initiation of incubation for pellets of the indicated polymer composition.
Figure 7:
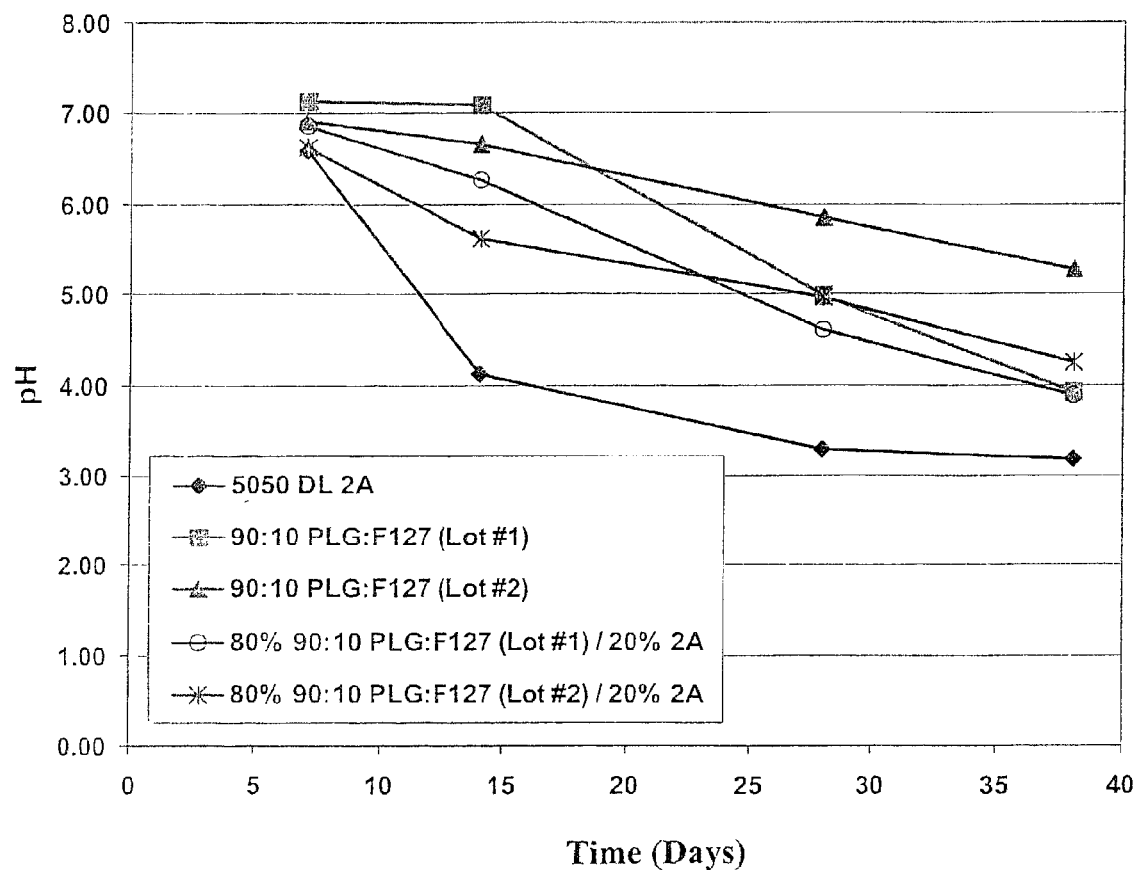
FIG. 7 is a graph of pH of the incubation solution for determination of mass loss of pellets versus time in days following initiation of incubation.
Figure 8:
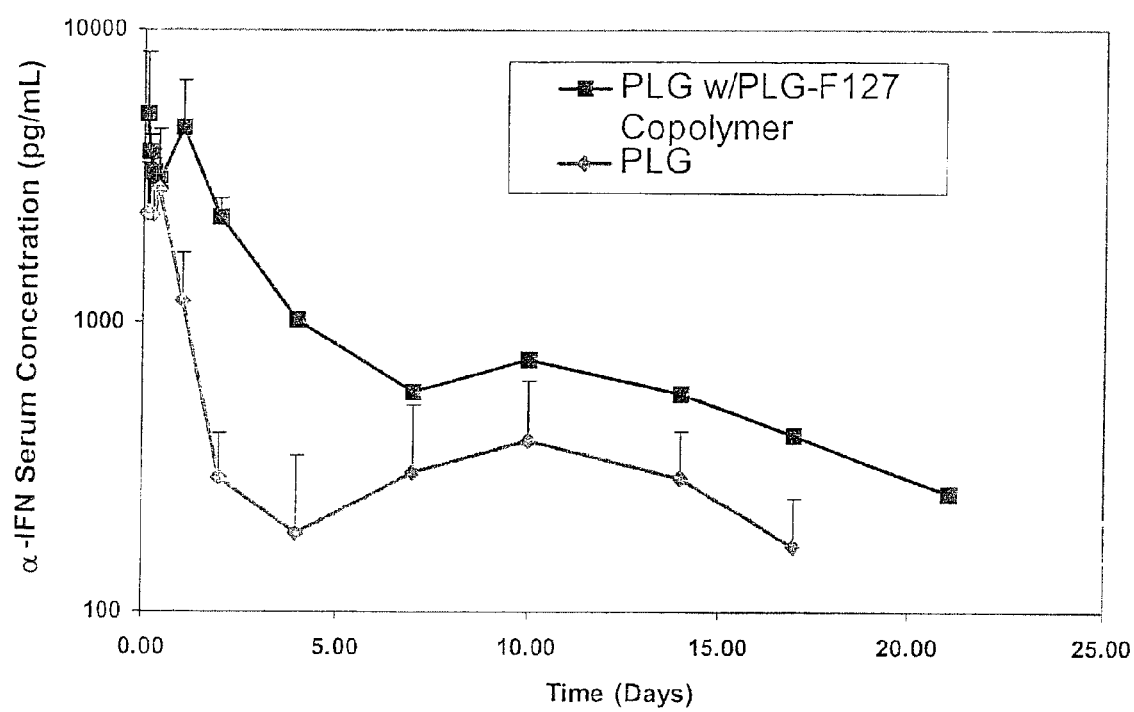
FIG. 8 is a graph of IFN serum concentration in rats versus time in days following administration of the indicated IFN-microparticle formulation.
Figure 9:
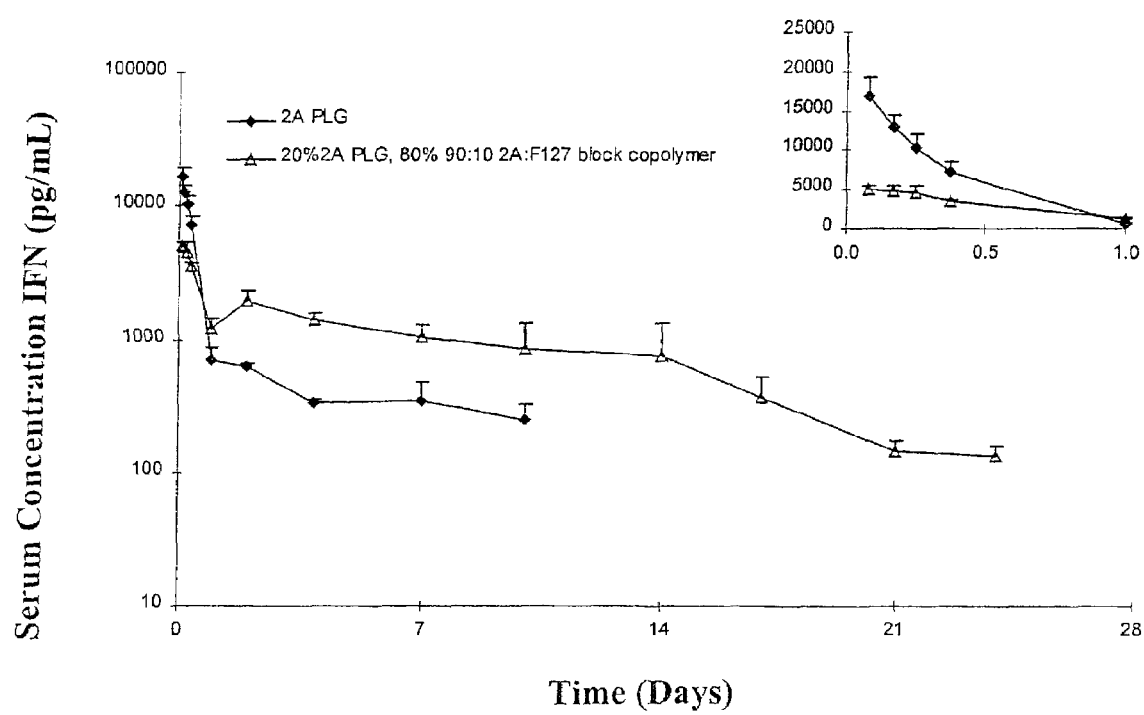
FIG. 9 is a graph of IFN serum concentration in rats versus time in days following administration of the indicated IFN-micropaticle formulation.

At each subsequent time point, (7, 14, 28 and 38 days) one pellet of each composition was removed from the buffer dried under vacuum for one day, and weighed again to determine the mass remaining. Also, the pH of the buffer from which the pellet was removed was measured. The results of these determinations are shown graphically in FIGS. 6 and 7, respectively.

The % Water Uptake after a 2 day incubation at 37° C. for the 2A, PLG:F127 triblock and PLG:F127 copolymer/2A blend was 34%, 15%, and 133% which corresponds to a water absorption ratio of 1.34, 1.15 and 2.33.

Preparation of α-LFN-Containing Microparticles

Materials:
Methylene Chloride
Ethanol
90:10 PLG/F127, prepared as described herein.
Alkermes 5050 DL 2A polymer, (PLG, 10 kD, acid end group)

Spray-frozen, lyophilized protein powder containing α-IFN, sucrose (1:1 ratio to the IFN), phosphate buffer (42% αIFN by weight)

Magnesium Carbonate

Preparation

To 216 mg of 90:10 PLG/F127 and 54 mg PLG was added 4.5 mL of methylene chloride to dissolve the polymers. The polymer solution was then added to 15 mg of the protein powder (Zn-complexed) to achieve about a 2% load of IFN, and the resulting suspension was sonicated for 3 min. to fragment the powder. Then 15 mg of magnesium carbonate powder (about 5% of the total weight of polymer, protein and excipient) was added and the suspension was sonicated another minute.

Next, the sonicated suspension was spray-frozen, using an ultrasonic nozzle, into a container with liquid nitrogen on a bed of frozen ethanol. The container was stored at −80° C. overnight, where the liquid nitrogen evaporated and the ethanol melted, leading to extraction of methylene chloride and curing of the polymer microparticles.

The resulting microparticles were harvested by cold filtration, then lyophilized to remove residual solvents. These dried microparticles were then sieved using a 125-μm mesh to obtain a fraction which could be easily injected through a 21 gauge needle.

Microparticles having the 5050 DL 2A Polymer alone and interferon incorporated therein, were also prepared. Briefly, the procedure set forth above was followed except that 270 mg of the 5050 DL 2A poly(lactide-co-glycolide) polymer alone in 3.5 mL of methylene chloride was employed.

The α-IFN-containing microparticles prepared as described above were tested in vivo as follows. Male Sprague-Dawley rats weighing approximately 450±50 grams (3 animals per group) were treated with 5 mg/kg Sandimmune Cyclosporine IP daily for days 0-14 post injection (except Sundays). The desired dose of microparticles in vehicle were injected into the interscapular region of the animals using a 1.0 cc syringe and a 21 gauge needle. The dose of microparticles was about 17 mg of microparticles suspended in 1.0 mL of a vehicle comprising 3.0% carboxymethyl cellulose (CMC), 0.9% NaCl, 0.1% Tween 20.

Blood samples were taken at 2, 4, 6, 9 and 24 hours and 2, 4, 7, 10, 14, 17, 21, 24 and 28 days. For some animals it was not possible to collect blood samples for every time point desired. The serum was separated and IFN concentration determined using ELISA as earlier described.

The results of the in vivo release profile of αIFN containing microparticles prepared as described above are set forth in FIG. 8 (data is dose normalized).

The microparticles prepared from the polymer blend of PLG and PLG:F127 block polymer resulted in a substantial reduction in the initial release of interferon in comparison to microparticles prepared in the same manner but using PLG alone. In addition, a substantial increase in serum levels during the sustained-release phase was seen for the animals receiving the interferon containing microparticles having the blended polymer in comparison to PLG alone. As a result, there was an approximate doubling of the area-under-the-curve (AUC) or bioavailability (61% for blend vs. 30% for PLG alone).

Microparticles prepared as described about but with $MgCO_3$ and lyophilized protein powder containing αIFN, sucrose (1:1 ratio), phosphate buffer (42% αIFN by weight) were prepared. As above, drug load in the microparticles ws a 2% with approximately 5% $MgCO_3$. The data are dose normalized to 1 mg/kg. The results of in vivo testing are shown in FIG. 9 (no zinc present with IFN).

While this invention has been particularly shown and described with references to preferred embodiments thereof, it will be understood by those skilled in the art that various changes in form and details may be made therein without departing from the scope of the invention encompassed by the appended claims.

What is claimed is:

1. A polymer blend composition comprising a hydrophobic biocompatible, biodegradable polymer and a biocompatible amphipathic polymer having a water absorption ratio of about 2 or less wherein the amphinathic polymer is a polyetherester.

2. The composition of claim 1 wherein the hydrophobic biocompatible, biodegradable polymer is selected from poly (lactides), poly(glycolides), poly(lactide-co-glycolides), poly(lactic acid)s, poly(glycolic acid)s polycarbonates, polyesteramides, polyanhydrides, polyorthoesters, poly(dioxanone)s, polycaprolactones, polyurethanes, polycyanoacrylates, blends thereof and copolymers thereof.

3. The composition of claim 2, wherein the hydrophobic biocompatible, biodegradable polymer is poly(lactide-co-glycolide).

4. The composition of claim 1, wherein the polyetherester polymer is a copolymer of polyethylene glycol and polybutylene terephthalate.

5. The composition of claim 4, wherein the copolymer of polyethylene glycol and polybutylene terephthalate is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

6. The composition of claim 1 wherein the amount of hydrophobic biocompatible, biodegradable polymer present in the polymer blend is from about 10% w/w to about 90% w/w of the total weight of the polymer blend.

7. The composition of claim 6, wherein the amount of hydrophobic biocompatible, biodegradable polymer present in the polymer blend is from about 20% w/w to about 80% w/w of the total weight of the polymer blend.

8. The composition of claim 1, wherein the amount of polyetherester in the polymer blend is from about 10% w/w to about 90% w/w of the total weight of the polymer blend.

9. The composition of claim 8, wherein the polyetherester present in the polymer blend is from about 20% w/w to about 80% w/w of the total weight of the polymer blend.

10. The composition of claim 8, wherein the amount of polyetherester present in the polymer blend is from about 10% wlw to about 50% w/w of the total weight of the polymer blend and is a polyethylene glycol/polybutylene terephthalate polymer.

11. The composition of claim 10, wherein the polyethylene glycol/polybutylene terephthalate polymer is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

12. A sustained release composition comprising a biologically active agent which is incorporated within a polymer blend comprising a hydrophobic biocompatible, biodegradable polymer and a biocompatible amphipathic polymer having a water absorption ratio of about 2 or less wherein the amphipathic polymer is a polyetherester.

13. The sustained release composition of claim 12 wherein the hydrophobic biocompatible, biodegradable polymer is selected from poly(lactides), poly(glycolides), poly(lactide-co-glycolides), poly(lactic acid)s, poly(glycolic acid)s polycarbonates, polyesteramides, polyanhydrides, polyorthoesters, poly(dioxanone)s, polycaprolactones, polyurethanes, polycyanoacrylates, blends thereof and copolymers thereof.

14. The sustained release composition of claim 13, wherein the hydrophobic biocompatible, biodegradable polymer is poly(lactide-co-glycolide).

15. The sustained release composition of claim 14, wherein the polyetherester polymer is a copolymer of polyethylene glycol and polybutylene terephthalate.

16. The sustained release composition of claim 15, wherein the copolymer of polyethylene glycol and polybutylene terephthalate is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

17. The sustained release composition of claim 12 wherein the amount of hydrophobic biocompatible, biodegradable polymer present in the polymer blend is from about 10% w/w to about 90% w/w of the total weight of the blend polymer.

18. The sustained release composition of claim 17, wherein the amount of hydrophobic biocompatible, biodegradable polymer present in the polymer blend is from about 20% w/w to about 80% w/w of the total weight of the polymer blend.

19. The sustained release composition of claim 12, wherein the amount of polyetherester present in the polymer blend is from about 10% w/w to about 90% w/w of the total weight of the polymer blend.

20. The sustained release composition of claim 19, wherein the amount of polyetherester present in the polymer blend is from about 20% w/w to about 80% w/w of the total weight of the polymer blend.

21. The sustained release composition of claim 19, wherein the amount of polyetherester present in the polymer blend is from about 10% w/w to about 50% w/w of the total weight of the polymer blend and is a polyethylene glycol/polybutylene terephthalate polymer.

22. The sustained release composition of claim 21, wherein the polyethylene glycol/polybutylene terephthalate polymer is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

23. The sustained release composition of claim 12, wherein the biologically active agent is present from about 0.01% (w/w) to about 50% (w/w) of the total weight of the composition.

24. The sustained release composition of claim 23, wherein the biologically active agent is present from about 0.1% to about 30% (w/w) of the total weight of the composition.

25. The sustained release composition of claim 12, which is in the form of microparticles.

26. The sustained release composition of claim 12, wherein the biologically active agent is a protein.

27. The sustained release composition of claim 12, wherein the polyetherester copolymer is a copolymer of polyethylene glycol and polybutylene terephthalate.

28. The sustained release composition of claim 27, wherein the copolymer of polyethylene glycol and polybutylene terephthalate is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

29. A method for the sustained delivery of a biologically active agent to a patient in need thereof comprising administering a therapeutically effective amount of a sustained release composition comprising a biologically active agent which is incorporated within a blend polymer comprising a hydrophobic biocompatible, biodegradable polymer and a biocompatible amphipathic polymer having a water absorption ratio of about 2 or less wherein the amphipathic polymer is a polyetherester.

30. The method of claim 29 wherein the hydrophobic biocompatible, biodegradable polymer is selected from poly (lactides), poly(glycolides), poly(lactide-co-glycolides), poly(lactic acid)s, poly(glycolic acid)s polycarbonates, polyesteramides, polyanhydrides, polyorthoesters, poly(dioxanone)s, polycaprolactones, polyurethanes, polycyanoacrylates, blends thereof and copolymers thereof.

31. The method of claim 30, wherein the hydrophobic biocompatible, biodegradable polymer is poly(lactide-co-glycolide).

32. The method of claim 29, wherein the polyetherester polymer is a copolymer of polyethylene glycol and polybutylene terephthalate.

33. The method of claim 32, wherein the copolymer of polyethylene glycol and polybutylene terephthalate is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

34. The method of claim 29 wherein the amount of hydrophobic biocompatible, biodegradable polymer present in the polymer blend is from about 10% w/w to about 90% w/w of the total weight of the polymer blend.

35. The method of claim 34, wherein the amount of hydrophobic biocompatible, biodegradable polymer present in the polymer blend is from about 20% w/w to about 80% w/w of the total weight of the polymer blend.

36. The method of claim 29, wherein the amount of polyetherester present in the polymer blend is from about 10% w/w to about 90% w/w of the total weight of the polymer blend.

37. The method of claim 36, wherein the amount of polyetherester present in the polymer blend is from about 20% w/w to about 80% w/w of the total weight of the polymer blend.

38. The method of claim 36, wherein the amount of polyetherester present in the polymer blend is from about 10% w/w to about 50% w/w of the total weight of the polymer blend and is a polyethylene glycol/polybutylene terephthalate polymer.

39. The method of claim 38, wherein the polyethylene glycol/polybutylene terephthalate polymer is selected from 300PEGT80PBT20, 300PEGT70PBT30, 300PEGT55PBT45, 600PEGT80PBT20, 1000PEGT60PBT40, 1000PEGT70PBT30, 1000PEGT80PBT20.

40. The method of claim 29, wherein the biologically active agent is present from about 0.01% (w/w) to about 50% (w/w) of the total weight of the composition.

41. The method of claim 40, wherein the biologically active agent is present from about 0.1% to about 30% (w/w) of the total weight of the composition.

42. The method of claim 29, wherein the sustained release composition is in the form of microparticles.

43. The method of claim 29, wherein the biologically active agent is a protein.

* * * * *